United States Patent [19]

Bickert

[11] Patent Number: 4,897,474

[45] Date of Patent: Jan. 30, 1990

[54] CARBOHYDRATE FATTY ACID ESTERS AND A PROCESS FOR PREPARING THEM

[75] Inventor: Peter Bickert, North Edison, N.J.

[73] Assignee: Huels Aktiengesellschaft, Marl, Fed. Rep. of Germany

[21] Appl. No.: 44,248

[22] Filed: Apr. 30, 1987

[30] Foreign Application Priority Data

Jul. 11, 1986 [DE] Fed. Rep. of Germany ....... 3623371

[51] Int. Cl.$^4$ ...................... C07C 69/33; C07C 67/62; C07C 69/58; C07H 13/06
[52] U.S. Cl. .................................. 536/119; 536/124; 260/398.5; 260/410; 260/410.6; 260/410.7
[58] Field of Search .............................. 536/119, 124; 260/398.5, 410, 410.7, 410.6

[56] References Cited

U.S. PATENT DOCUMENTS

| | | | |
|---|---|---|---|
| 4,268,498 | 5/1981 | Gedeon et al. | 536/119 |
| 4,297,290 | 10/1981 | Stockburger | 536/119 |
| 4,517,360 | 5/1985 | Volpenhein | 536/119 |
| 4,518,772 | 5/1985 | Volpenhein | 536/119 |

*Primary Examiner*—Ronald W. Griffin
*Attorney, Agent, or Firm*—Oblon, Spivak, McClelland, Maier & Neustadt

[57] ABSTRACT

The invention concerns carbohydrate fatty acid esters with improved color and free-flow properties and a one-step process for preparing them. To prepare the products, carbohydrates are esterified with fatty acids in the presence of polyether polyols.

14 Claims, No Drawings

CARBOHYDRATE FATTY ACID ESTERS AND A PROCESS FOR PREPARING THEM

BACKGROUND OF THE INVENTION

1. Field of the Invention:

The invention concerns carbohydrate fatty acid esters that are improved with regard to color and ease of handling, and a one-step process for preparing them.

2. Discussion of the Background:

Carbohydrate fatty acid esters and processes for preparing them are known. They can be prepared according to European Patents 0 132 293 and 0 132 941 by the transesterification of fatty acid esters of short-chained alcohols with a saccharide or a sugar alcohol. Processes are also known by which a direct esterification of carbohydrates is carried out with free fatty acids. Sorbitan fatty acid esters are prepared by direct esterification according to U.S. Pat. No. 4,297,290. According to this patent, anhydrosorbitol is first prepared from sorbitol with acid catalysis, and is then reacted with a fatty acid with alkaline catalysis. The color of the products is improved by treatment with activated charcoal, phosphoric acid, and diatomaceous earth.

Therefore, either an esterification and a transesterification are carried out, or an anhydrosugar is prepared and an esterification is carried out. These processes, therefore, require at least two reaction steps, with any optional treatment with activated charcoal, especially in the case of highviscosity products, representing another difficult process step.

According to German OS 31 19 553, carboxylic acid esters of anhydrohexitols are prepared by reacting hexitols, preferably sorbitol, with carboxylic acids using alkaline catalysis at 210°–260° C., and then treating the products with hydrogen peroxide.

However, this one-step process provides products that are not fully satisfactory for use as emulsifiers in high-quality cosmetics or foods with regard to clarity, color, and free-flow properties, especially when partially hydrogenated starch hydrolyzates are reacted with fatty acids.

SUMMARY OF THE INVENTION

Accordingly, an object of this invention is to provide a simple process for preparing carbohydrate fatty acid esters with good color quality and low turbidity.

Another object is to provide carbohydrate fatty acid esters with improved ease of handling and improved free-flow properties.

These object and other objects of the invention which will become apparent from the following specification have been achieved by the present carbohydrate fatty acid esters having improved color and free-flow properties, comprising a content of from 1–15 wt. % polyether polyol, and by the process for preparing the carbohydrate fatty acid esters comprising reacting with alkaline catalysis (a) a carbohydrate, (b) a fatty acid, (c) a color improver and (d) from 1–15 wt. % of a polyether polyol based on the total amount of reactants used; and bleaching the product of said reacting step.

DETAILED DESCRIPTION OF THE PREFERRED EMBODIMENTS

It has now been found that carbohydrate fatty acid esters with improved color and reduced viscosity are obtained when 1 to 15 wt. % of a polyether polyol based on the total amount of the reaction components is added to the esterification mixture of carbohydrate and fatty acid, an effective amount of hypophosphite is added as a color improver and the reaction mixture is bleached with hydrogen peroxide after the completion of the reaction.

Suitable polyether polyols are polyethylene glycol, polypropylene glycol, or polyglycerin. Polyglycerins with average degrees of polymerization of 2 to 5 are preferably used.

Monomeric glycerin with a degree of polymerization of 1 has only a slight, inadequate effect on the improvement of the color and the lowering of the viscosity. Mixtures of polyglycerins with cyclic polyether polyols such as those described in German OS 21 33 281, for example, can also be used.

The polyether polyols are preferably used at concentrations of about 4 to 10 wt. % based on the total amount of the reaction components. The polyether polyols are admixed with the starting materials or are added during the esterification reaction.

Preferred carbohydrates for the esterification are sugar alcohols with 5 or 6 carbon atoms. Examples of hexitols include sorbitol, mannitol, and dulcitol. Suitable pentitols include arabitol, ribitol, xylitol, and lyxitol.

Preferred fatty acids are carboxylic acids with 6 to 30 carbon atoms. The fatty acids may also contain double bonds in the carbon chain. Examples included are octanoic acid, decanoic acid, dodecanoic acid, oleic acid, palmitic acid, stearic acid, coconut oil fatty acid, and rapeseed oil fatty acid.

Coconut oil fatty acid consists of a mixture of caproic acid, caprylic acid, capric acid, lauric acid, myristic acid, palmitic acid, palmitoleic acid, stearic acid, oleic acid, elaidic acid, and linoleic acid.

The main components of rapeseed oil fatty acid are caprylic acid, capric acid, lauric acid, myristic acid, palmitic acid, palmitoleic acid, stearic acid, oleic acid, elaidic acid, linoleic acid, arachidonic acid, gadoleic acid, behenic acid, and erucic acid.

The esterification reaction is carried out at from 180° to 250° C., preferably from 190° to 220° C. The reaction time is generally from about 2 to 10 hours.

Examples of suitable catalysts include KOH, NaOH, $Na_2CO_3$.

A color improver is added during the reaction, preferably at the very beginning of the reaction. Suitable color improvers are hypophosphites such as calcium or sodium hypophosphite or hypophosphorous acid. They are used at concentrations of 0.1 to 0.5 wt.% based on the total amount of the reaction components used.

Hydrogen peroxide is generally used as the bleach, and is added after the reaction at temperatures of 70° to 85° C. in a proportion of 0.1 to 1.5 wt. % based on the total amount of reaction components used.

The products produced by the process of the present invention are distinguished from carbohydrate fatty acid esters prepared by conventional processes by a lighter color, less cloudiness, lower acid number, and improved free-flow characteristics.

Carbohydrate fatty acid esters are surface-active compounds that are used particularly as emulsifiers in the cosmetics and food sectors, but also as polymerization adjuvants and slip additives. A special benefit of the present process is the fact that after the addition of polyglycerin, esters are formed from polyglycerin and fatty acids in the course of the reaction, that likewise belong to the group of surfaceactive compounds. These esters are already known as food emulsifiers.

Other features of the invention will become apparent in the course of the following descriptions of exemplary embodiments which are given for illustration of the invention and are not intended to be limiting thereof.

EXAMPLES

EXAMPLE 1

A 30-liter stirred kettle with distillation attachment, thermocouple, and a nitrogen inlet at the base of the kettle is charged under stirring with 10.79 kg (38.5 moles) of rapseed oil fatty acid, 0.14 kg (3.5 moles) of powdered NaOH, 4.56 kg (17.5 moles) of 70% aqueous sorbitol solution, 0.71 kg (5 wt. %) of polyglycerin with an average degree of polymerization of 3, and 0.037 kg (0.25 mole) of sodium hypophosphite. The mixture is heated while a stream of nitrogen is passed through it. Water distills off at 100° C. and above. After reaching 200° C., this temperature is held until a sample withdrawn shows an acid number AN less than 2. The temperature is then lowered to 80° C. and the reaction batch is bleached by adding 87 g of 30% hydrogen peroxide dropwise over a period of 30 min. Finally, the stirring is continued for 1 hour longer at 85° C. and the product is discharged. The product properties are summarized in Table 1.

Examples 2 to 7, Comparison Examples A to G

The process of Example 1 is repeated. The substances used, their quantities, and the properties of the resulting carbohydrate fatty acid esters, are summarized in Table 1.

without consideration of the actual molecular weight distribution.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A carbohydrate fatty acid ester-polyether polyol with improved color and free-flow properties, comprising a carbohydrate fatty acid ester containing from 1–15 wt. % of a polyether polyol.

2. The carbohydrate fatty acid ester of claim 1, wherein said polyether polyol is a member selected from the group consisting of polyethylene glycols, propylene glycols, and polyglycerins.

3. The carbohydrate fatty acid ester of claim 2, wherein said polyether polyol is a polyglycerin.

4. The carbohydrate fatty acid ester of claim 3, wherein said polyglycerin has an average degree of polymerization of from 2–5.

5. The carbohydrate fatty acid ester of claim 1, wherein said carbohydrate fatty acid ester comprises (i) a carbohydrate portion comprising at least one sugar alcohol with 5–6 carbon atoms, and (ii) a fatty acid portion comprising at least one carboxylic acid with 6–30 carbon atoms.

6. The carbohydrate fatty acid ester of claim 5, wherein said sugar alcohol is a member selected from the group consisting of sorbitol, mannitol, dulcitol, arabitol, ribitol, xylitol and lyxitol.

7. The carbohydrate fatty acid ester of claim 5,

TABLE 1

| No. | REACTANTS Carbohydrate | g | Fatty acid | g | Molar Ratio | PG g | CONDITIONS Temp. °C. | Time hr. | PRODUCTS CN | AN | EN | OHN | H₂O % | State/Description at room temperature |
|---|---|---|---|---|---|---|---|---|---|---|---|---|---|---|
| A | Sorbitol (70%) | 456 | Rapeseed | 1,079 | 1:2.2 | — | 200 | 6 | 7 | 4 | 136 | 178 | 0.3 | Cloudy, pourable |
| 1 | Sorbitol (70%) | 456 | Rapeseed | 1,079 | 1:2.2 | 70 | 200 | 6 | 4 | 4 | 133 | 231 | 0.3 | Clear, readily pourable |
| B | Sorbitol (70%) | 456 | Coconut | 781 | 1:2.2 | — | 200 | 5 | 2 | 4 | 172 | 221 | 0.2 | Solid |
| 2 | Sorbitol (70%) | 456 | Coconut | 781 | 1:2.2 | 56 | 200 | 5 | 2 | 4 | 167 | 277 | 0.4 | Clear, readily pourable |
| C | Sorbitol | 319 | Coconut | 781 | 1:2.2 | — | 200 | 5 | 2 | 3 | 172 | 212 | 0.2 | Solid |
| 3 | Sorbitol | 319 | Coconut | 781 | 1:2.2 | 56 | 200 | 4 | 2 | 6 | 167 | 286 | 0.3 | Limited free-flow |
| D | Sorbitol (70%) | 456 | Coconut | 781 | 1:2.2 | — | 225 | 5 | 7 | 3 | 106 | 189 | 0.3 | Solid, pourable only |
| 4 | Sorbitol (70%) | 456 | Coconut | 781 | 1:2.2 | 56 | 225 | 3 | 4 | 4 | 172 | 222 | 0.1 | Slightly flakey |
| E | M-Glucoside | 300 | Rapeseed | 883 | 1:2.2 | — | 200 | 10 | 100 | 11 | 140 | 150 | 3.0 | Slightly cloudy, pourable, dark |
| 5 | M-Glucoside | 300 | Rapeseed | 883 | 1:2.2 | 60 | 200 | 10 | 35 | 11 | 139 | 202 | 3.1 | Clear, pourable |
| F | PGS III | 562 | Rapeseed | 1,079 | 1:1.1 | — | 200 | 6 | 20 | 18 | 133 | 219 | 3.9 | Cloudy, pourable, sediment |
| 6 | PGS III | 410 | Rapeseed | 771 | 1:1.1 | 60 | 200 | 3 | 20 | 13 | 121 | 245 | 3.6 | Clear, pourable, sediment |
| G | PGS II | 1,396 | Rapeseed | 668 | 4:1.1 | — | 200 | 3 | 80 | 14 | 71 | 627 | 7.8 | Solid, rubbery |
| 7 | PGS II | 1,047 | Rapeseed | 501 | 4:1.1 | 78 | 200 | 3 | 80 | 12 | 73 | 450 | 12.3 | Pourable |

Abbreviations used in the Table:
CN = Iodine color number
AN = Acid number in mg KOH/g
EN = Ester number in mg KOH/g
OHN = Hydroxyl number in mg KOH/g
PG = Polyglycerin, average degree of polymerization 3, composition:
16% mono-, 25% di-, 24% tri-, 19% tetra-, 9% penta-, 7% hexaglycerin
M Glucoside = Alpha-methylglucoside
PGS III = Polyglucosylsorbitol, average degree of polymerization 2 to 3 70% aqueous solution
PGS II = Polyglucosylsorbitol, average degree of polymerization 12, 70% aqueous solution In the case of the higher molecular weight carbohydrates (polyglucosylsorbitols), the molar ratios indicated refer to the amount of fatty acid per glucosyl unit wherein said carboxylic acid is a member selected from the group consisting of octanoic acid, decanoic acid, dodecanoic acid, oleic acid, palmitic acid, stearic acid, coconut oil fatty acid, and rapeseed oil fatty acid.

8. A process for preparing a carbohydrate fatty acid ester,-polyether polyol with improved color and free-flow properties, comprising the steps of:
reacting (a) a carbohydrate, (b) a fatty acid, (c) a color improver and (d) from 1-15 wt. % of a polyether polyol based on the total amount of reactants used, in the presence of an alkaline catalyst; and
bleaching the product of said reacting step.

9. The process of claim 8, wherein said color improver is a hypophosphite or hypophosphorous acid.

10. The process of claim 9, wherein said color improver is calcium or sodium hypophosphite.

11. The process of claim 8, wherein said bleaching step is performed by adding hydrogen peroxide.

12. The process of claim 8, wherein said polyether polyol is a polyglycerin with an average degree of polymerization of from 2-5.

13. The process of claim 12, wherein about 4-10 wt. % of said polyglycerin is used based on the amount of carbohydrate.

14. The process of claim 8, wherein said reacting step is carried out at temperatures from about 190°-220° C.

* * * * *